United States Patent [19]

Heath et al.

[11] Patent Number: 6,113,948
[45] Date of Patent: Sep. 5, 2000

[54] MICROPARTICLES AND THEIR USE IN WOUND THERAPY

[75] Inventors: David Heath; Sarah Margaret Middleton, both of Nottingham, United Kingdom

[73] Assignee: Quadrant Healthcare, Nottingham, United Kingdom

[21] Appl. No.: 08/858,814

[22] Filed: May 19, 1997

[51] Int. Cl.$^7$ .................................................. A61K 9/64
[52] U.S. Cl. .................. 424/499; 424/489; 424/490; 424/493
[58] Field of Search ............... 424/46, 45, 489, 424/490, 493, 499

[56] References Cited

U.S. PATENT DOCUMENTS

| | | | |
|---|---|---|---|
| 3,565,559 | 2/1971 | Sato et al. | 424/37 |
| 3,960,583 | 6/1976 | Netting et al. | 106/122 |
| 4,427,651 | 1/1984 | Stroetmann | 424/46 |
| 4,752,466 | 6/1988 | Saferstein et al. | 424/46 |
| 5,145,684 | 9/1992 | Liversidge et al. | 424/489 |
| 5,663,198 | 9/1997 | Reul et al. | 514/471 |

FOREIGN PATENT DOCUMENTS

| | | |
|---|---|---|
| 0 086 627 A1 | 8/1983 | European Pat. Off. . |
| 0 172 710 A2 | 2/1986 | European Pat. Off. . |
| 0 196 813 A1 | 10/1986 | European Pat. Off. . |
| 0 444 692 A1 | 9/1991 | European Pat. Off. . |
| 0 494 417 A2 | 7/1992 | European Pat. Off. . |
| 0 681 843 A2 | 11/1995 | European Pat. Off. . |
| 60-214728 | 10/1985 | Japan . |
| 3-201982 | 9/1991 | Japan . |
| 8-53365 | 2/1996 | Japan . |
| WO 91/12823 | 9/1991 | WIPO . |
| WO 92/13495 | 8/1992 | WIPO . |
| WO 92/18164 | 10/1992 | WIPO . |
| WO 94/08627 | 4/1994 | WIPO . |
| WO 95/31479 | 11/1995 | WIPO . |
| WO 96/09814 | 4/1996 | WIPO . |
| WO 96/18388 | 6/1996 | WIPO . |

OTHER PUBLICATIONS

Coller, B.S., et al., "Thromboerythrocytes: In Vitro Studies of a Potential Autologous, Semi-artificial Alternative to Platelet Transfusions," *J. Clin. Invest.* 89:546–555 (1992).
English Language Abstract of Japanese Patent No. 60-214728 A (Document AM1).
English Language Abstract of Japanese Patent No. 3-201982 A (WPI/Derwent, Accession No. 91-300974) (Document AP1).
English Language Abstract of Japanese Patent No. 8-53365 A (WPI/Derwent, Accession No. 96-175677) (Document AN3), 1996.

Primary Examiner—Jose' G. Dees
Attorney, Agent, or Firm—Morrison & Foerster, LLP

[57] ABSTRACT

Soluble microparticles comprising fibrinogen or thrombin, in free-flowing form. These microparticles can be mixed to give a dry powder, to be used as a fibrin sealant that is activated only at a wound site.

10 Claims, No Drawings

MICROPARTICLES AND THEIR USE IN WOUND THERAPY

FIELD OF THE INVENTION

This invention relates to microparticles that may be produced by spray-drying, and to their therapeutic use. In particular, the invention relates to fibrin sealant.

BACKGROUND OF THE INVENTION

Fibrin sealant is a biological adhesive composed of fibrinogen and thrombin which is used extensively to assist wound healing and to provide sutureless closure of surgical wounds. Fibrinogen is the main structural protein in blood, responsible for forming clots.

For clot formation to occur, fibrinogen must be proteolytically cleaved and converted into fibrin monomer by thrombin, a serine protease that is converted to its active form by Factor Xa. Fibrin monomers assemble into fibrils and eventually form fibres in a three-dimensional network. The formation of a clot also requires the activity of Factor XIII. Factor XIII is a serine protease which is converted to its active form by thrombin in the presence of calcium. Activated Factor XIII (FXIIIa) then converts the non-covalent bonds between the assembled fibrin monomers into covalent bonds by transamination. This renders the fibrin gel less susceptible to proteolytic digestion by plasmin and also increases the overall strength and stiffness of the gel. Fibrin gel is readily resorbed by enzymatic and phagocytic pathways.

To reproduce this coagulation process in the form of a biological adhesive, the fibrinogen component of fibrin sealant usually contains Factor XIII, and the thrombin component is prepared in calcium chloride solution. The two components are applied either sequentially or simultaneously to the repair site, typically by syringe or by spraying. Fibrin sealant readily adheres to wet surfaces and, once polymerised, becomes a semi-rigid, haemostatic, fluid-tight adhesive capable of holding tissues or materials in the desired configuration.

Currently, fibrin sealant products are applied to the wound site as solutions, e.g. using a dual syringe device, which mixes the fibrinogen and thrombin as they exit. The main drawback of such delivery systems is clot formation within the device, resulting in needle and tube blockages. The dual syringe systems are also awkward to fill and manipulate. Further, if there is inadequate mixing of the fibrinogen and thrombin solutions, only weak clots may form.

Many wound sites ooze, and this can result in significant accumulation of fluid at the site. When solutions of the components of fibrin sealant are applied to such sites, they are often flushed away.

U.S. Pat. No. 4,427,651 discloses a sprayable preparation for accelerated haemostasis and optimised biochemical control of wound closure, containing a powdery mixture of 15–60% by weight of thrombin, 5–80% by weight of a desiccating and stabilising agent (albumin, globulin and/or fibrinogen), and 1–10% by weight of fibrinolysis inhibitor. The powdery mixture is suspended in a low-boiling, anhydrous solvent which is used as a propellant.

WO-A-9213495 discloses a lyophilised fibrinogen powder prepared by precipitation, without control of particle size. The powder is usually hydrated prior to use, with the disadvantages described above. It is also proposed that the powder can be used directly when the vessel or wound to be closed is small, and the blood loss is not rapid. In this case, the reaction is dependent on the presence of endogenous thrombin. In larger wounds, the heavier blood flow will wash away the endogenous material, and clotting will not take place.

SUMMARY OF THE INVENTION

It has now been realised that spray-drying is useful as a means to give novel, soluble microparticles (including microcapsules) comprising fibrinogen or thrombin.

Respective fibrinogen-containing and thrombin-containing soluble microparticles can be formulated together, in stable, dry form. This formulation can be subsequently activated, as desired, to give a fibrin sealant that is useful in wound therapy and surgical repair. It can meet the primary objectives of achieving good flow properties, enhanced, effective delivery to the active site, and dissolution only at the site, not in the delivery system.

DESCRIPTION OF THE INVENTION

Microparticles comprising fibrinogen or thrombin may be prepared by the procedures described in WO-A-9218164, WO-A-9609814 and WO-A-9618388. These spray-drying and associated particle manipulation processes enable the production of soluble protein microcapsules with defined size distribution, e.g. of up to 50 μm in diameter. For example, as described in those documents, the microparticles may be produced reproducibly, e.g. with 90% or more (by mass) up to 20 μm, e.g. 1 to 10 μm, or up to 5 μm, in size, or of submicron size if desired.

Microparticles of the invention may be prepared by spray-drying a solution of the active component alone. An alternative procedure comprises co-spray-drying, in which fibrinogen or thrombin and another wall-forming material are formulated and spray-dried, to give a microparticle in which the active component is incorporated in the wall of the particle.

The fibrinogen or thrombin may be full-length or any active fragment thereof. Fragments are known; see Coller et al, J. Clin. Invest. 89:546–555 (1992). Fibrinogen raw material may be a frozen solution, although a lyophilised powder which requires reconstitution prior to spray-drying may be used.

The spray-drying of proteins in the presence of excipients such as sugars (e.g. sucrose, lactose or mannitol) or other proteins stabilises the protein of interest and also ensures its effective dilution where low doses are required. The sugar may have a beneficial effect, in wound therapy.

Suitable other proteins may be naturally-occurring or recombinant. They may act as "wall-forming materials", as described in WO-A-9218164, where various examples are given. A preferred material is HSA (human serum albumin). For example, fibrinogen is spray-dried alone or in the presence of varying amounts of excipients such as HSA (e.g. fibrinogen: HSA ratios of 1:1, 1:3, 3:1) and sugars (e.g. mannitol).

The microparticles of this invention may have the physical characteristics described in the three publications identified above, e.g. being smooth and spherical, although size is not so critical since respirability is not a consideration. Known conditions can be used to produce, for example, microparticles of, say, c. 1.5 μm or c. 10 μm diameter, which can ensure optimum recovery of either of the two proteins of interest.

It has been found that microparticles produced by spray-drying fibrinogen are surprisingly active and soluble. The use of spray-dried fibrinogen preparations may therefore be particularly advantageous in the hospital setting, where the solubilisation of freeze-dried fibrinogen can take 15 minutes or more, and usually requires heating. This is a rate-limiting step, and can cause considerable delay in the administration of fibrin sealant preparations to patients.

The concentration of the thrombin component in fibrin sealant is relatively low (e.g. 150 μg thrombin per 40 mg fibrinogen). Preferably, therefore, thrombin is spray-dried with excipients such as HSA, sucrose, lactose or mannitol in varying proportions. This provides a homogeneous formulation, as described in more detail in Calcium ion, e.g. as calcium chloride, may be incorporated in the thrombin feedstock. Alternatively, calcium chloride may be added to the microcapsules after processing.

Microparticles of the invention may be sterilised, if necessary or desired. Sterile processing, γ-irradiation and ethylene oxide are examples of suitable techniques.

Although the components of the microcapsules in a fibrin sealant of the invention are preferably water-soluble, and the microparticles are preferably obtained by spray-drying a suitable solution, the microparticles that are obtainable may be free-flowing, discrete and substantially anhydrous. This means that the components of fibrin sealant in accordance with this invention are not activated until they are wetted, e.g. by coming into contact with liquid at a wound site. The active components may therefore be delivered as a dry mixture, although separate application of the different microparticles is also envisaged.

A dry powder fibrin sealant product may be of particular value where application to a large surface area is required. This includes surgery and repair of traumatic injuries to various organs such as the liver and spleen. A further advantageous application is in skin grafting for burns patients, and specifically where skin epidermal sheets are cultured in vitro and then transferred to the wound site. The use of fibrin sealant in the latter indication has proved to be particularly effective in patients with extensive burns, providing a biocompatible anchorage for skin grafts. It may also be suitable in the treatment of topical ulcers.

Products of the invention may be substantially dry. This means that they can be formulated with absorbent materials which, inter alia, can have the advantage over liquid fibrin sealants of drying and concentrating the product at the site of action, e.g. for haemostasis. A suitable such material is carboxymethylcellulose.

A NO scavenger may also be included in the formulation or, more generally, any material that promotes the aggregation of clots, inhibits their breakdown, or inhibits fibrin lysis. A material such as albumin has SH groups. These may remove NO from the site of aggregation, and thus increase clot formation.

As described in more detail in WO-A-9609814, spray-dried microparticles may retain functional groups available for the binding of therapeutic agents. In this invention, a drug may be bound to the microparticles, if desired at the site of application. Thus, for example, a cytotoxic drug may be used where it is desired to treat skin cancer.

Other drugs that may be included in products of the invention, e.g. those containing fibrinogen, are coagulation factors such as Factors VII, VIII, IX, X and XIII, and von Willebrand's factor. This may be incorporated by co-spray-drying.

It has recently been observed that denatured albumin microbubbles preferentially attach themselves to damaged endothelium. This suggests that products of the invention will accumulate at wound sites, not only because of the activation of fibrinogen but also if there is an albumin component of the microparticle.

The following Example illustrates the invention.

EXAMPLE

A fibrin sealant was prepared. This comprised a dry powder blend of microparticles respectively comprising fibrinogen and thrombin.

Fibrinogen (SNBTS) was formulated with 600 mg sucrose. Spray-drying was performed using a Mini Spray Dryer with a collecting vessel. The conditions were as follows:

| | |
|---|---|
| Inlet Temperature: | 100° C. |
| Outlet Temperature: | 65° C. |
| Atomisation Pressure: | 1.0 bar |
| Atomisation Type: | Schlick 970/0 |
| Feed Rate: | 1 g/min |

A 20% final excipient loading was achieved. The activity detected using a kinetic assay was 13.88 mg/100 mg. The theoretical activity is 10 mg/100 mg. This indicated full retention of the fibrinogen bioactivity.

Separately, 1 g D-mannitol (Roquette, ESEX4) was dissolved in 10 ml of 40 mM $CaCl_2$. The resultant solution was used to reconstitute 1 vial of thrombin (SNBTS). The spray-drying conditions used were as above, except that the outlet temperature was c. 62° C., and the feed rate was reduced to 0.75 g/min.

A thrombin clotting assay revealed a thrombin activity of 91.86 units/100 mg. This compared favourably with the theoretical activity, of 93 units/100 mg.

The respective microparticles containing fibrinogen and thrombin were mixed to form a 50:50 blend, in a glass vial. The vial was placed on a roller mixer for 20 min.

The blend was evaluated in a meat adhesion assay, in various blend sizes. Each assay requires two sections of liver (2.5 cm×2.5 cm). One liver section is stapled to a piece of cardboard. Both sections are wrapped in aluminium foil and incubated at 37° C. for 20 minutes.

The loose liver section is threaded with cotton. A solution of 5% human serum albumin is applied to the surface of both liver sections, followed by the dry powder blend of fibrinogen and thrombin (fibrin sealant). The two liver sections are placed together and incubated at 37° C. for 10 minutes.

The liver sections are then suspended from a clamp, and a hook is attached to the cotton. Weights are placed on the hook and the total weight suspended is used to calculate the tensile strength of the dry powder fibrin sealant blend in $mg/mm^2$. Results are given in the following Table.

| Blend Size (mg) | Fibrinogen (mg) | Thrombin (units) | Tensile Strength ($mg/mm^2$) |
|---|---|---|---|
| 0 | 0 | 0 | 0 |
| 100 | 5 | 45 | 29.6 |
| 200 | 10 | 90 | 23.7 |
| 300 | 15 | 135 | 36.0 |
| 400 | 20 | 180 | 46.4 |
| 500 | 25 | 225 | 50.6 |

We claim:

1. Soluble microcapsules having walls comprising fibrinogen or thrombin, said microcapsules being in free-flowing form.

2. Microcapsules according to claim 1, comprising thrombin and also calcium ion.

3. Microcapsules according to claim 1, comprising fibrinogen.

4. Microcapsules according to any of claims 1–3, produced by spray-drying.

5. Microcapsules according to any of claims 1–3, comprising albumin as a wall-forming material.

6. Microcapsules according to any of claims 1–3, additionally comprising a carbohydrate.

7. Microcapsules according to any of claims 1–3, up to 50 µm in size.

8. Microcapsules according to claim 7, of which at least 90% by mass are 10 to 20 µm in size.

9. A dry mixture of soluble microcapsules according to any of claims 1–3, respectively containing fibrinogen and thrombin.

10. A product comprising first and second microcapsules according to any of claims 1 to 3, respectively containing fibrinogen and thrombin, as a combined preparation for simultaneous use in wound therapy or surgical repair.

* * * * *